(12) United States Patent
Zhao et al.

(10) Patent No.: US 10,119,917 B2
(45) Date of Patent: Nov. 6, 2018

(54) APPARATUS AND METHOD FOR BIDIRECTIONAL RAMAN SPECTROSCOPY

(71) Applicants: Jun Zhao, The Woodlands, TX (US); Xin Jack Zhou, Hockessin, DE (US); Sean Xiaolu Wang, Wilmington, DE (US)

(72) Inventors: Jun Zhao, The Woodlands, TX (US); Xin Jack Zhou, Hockessin, DE (US); Sean Xiaolu Wang, Wilmington, DE (US)

(73) Assignee: B & W Tek LLC, Newark, DE (US)

( * ) Notice: Subject to any disclaimer, the term of this patent is extended or adjusted under 35 U.S.C. 154(b) by 0 days.

(21) Appl. No.: 15/653,636

(22) Filed: Jul. 19, 2017

(65) Prior Publication Data

US 2018/0136138 A1 May 17, 2018

Related U.S. Application Data

(63) Continuation-in-part of application No. 15/461,613, filed on Mar. 17, 2017, which is a continuation-in-part of application No. 15/378,156, filed on Dec. 14, 2016, which is a
(Continued)

(51) Int. Cl.
| | | |
|---|---|---|
| *G01N 21/65* | (2006.01) | |
| *G01N 33/15* | (2006.01) | |
| *G01J 3/10* | (2006.01) | |
| *G01J 3/02* | (2006.01) | |

(52) U.S. Cl.
CPC ............ *G01N 21/658* (2013.01); *G01J 3/021* (2013.01); *G01J 3/0229* (2013.01); *G01J 3/10* (2013.01); *G01N 33/15* (2013.01); *G01J 2003/102* (2013.01)

(58) Field of Classification Search
CPC ...... G01J 2003/102; G01J 3/44; G01J 3/4412; G01J 21/65; A61B 5/0075
See application file for complete search history.

(56) References Cited

U.S. PATENT DOCUMENTS

| | | |
|---|---|---|
| 4,076,421 A | 2/1978 | Kishner |
| 4,378,159 A | 3/1983 | Galbraith |
| 4,645,340 A | 2/1987 | Graham et al. |

(Continued)

FOREIGN PATENT DOCUMENTS

| | | |
|---|---|---|
| DE | 26 06 675 B2 | 6/1978 |
| DE | 33 11 954 A1 | 3/1984 |

(Continued)

OTHER PUBLICATIONS

English language translation of German Office Action of German Applicaton No. 102016225808.7, dated Nov. 24, 2017.

*Primary Examiner* — Michael P LaPage

(57) ABSTRACT

This invention relates to an apparatus and method for performing bidirectional Raman spectroscopy of a sample, preferably a diffusely scattering sample, in which two excitation light sources are employed to illuminate the sample from two opposite directions to excite Raman scattering signal from the sample. The Raman scattering signal which transmits through the sample are collected by two optical devices each positioned on the opposite side of the sample to obtain two transmission Raman spectra of the sample, which enables the accurate determination of the composition of the whole sample.

14 Claims, 3 Drawing Sheets

Related U.S. Application Data continuation-in-part of application No. 15/349,510, filed on Nov. 11, 2016.

(56) References Cited

U.S. PATENT DOCUMENTS

| | | | |
|---|---|---|---|
| 4,853,542 A | 8/1989 | Milosevic et al. | |
| 4,988,205 A | 1/1991 | Snail | |
| 5,112,127 A | 5/1992 | Carrabba et al. | |
| 5,199,431 A | 4/1993 | Kittrell et al. | |
| 5,280,788 A | 1/1994 | Janes et al. | |
| 5,517,315 A | 5/1996 | Snail et al. | |
| 5,615,673 A * | 4/1997 | Berger | A61B 5/14532 356/301 |
| 5,625,458 A * | 4/1997 | Alfano | A61B 5/0059 356/446 |
| 5,659,397 A | 8/1997 | Miller et al. | |
| 5,864,397 A | 1/1999 | Vo-Dinh | |
| 5,946,090 A * | 8/1999 | Tashiro | G01J 3/10 356/301 |
| 6,370,406 B1 | 4/2002 | Wach et al. | |
| 6,781,697 B1 | 8/2004 | Carra et al. | |
| 7,148,963 B2 | 12/2006 | Owen et al. | |
| 7,652,763 B2 | 1/2010 | Matousek et al. | |
| 7,671,985 B1 | 3/2010 | Milosevic et al. | |
| 8,085,396 B2 | 12/2011 | Matousek et al. | |
| 8,248,600 B2 | 8/2012 | Matousek et al. | |
| 2003/0120137 A1 * | 6/2003 | Pawluczyk | A61B 5/14532 600/310 |
| 2004/0263842 A1 | 12/2004 | Puppets | |
| 2006/0238745 A1 * | 10/2006 | Hashimoto | G01J 3/44 356/73 |
| 2007/0121119 A1 * | 5/2007 | Martinez | G01J 3/44 356/489 |
| 2008/0259345 A1 * | 10/2008 | Fukutake | G02B 21/18 356/450 |
| 2009/0231578 A1 * | 9/2009 | Ling | A61B 5/0075 356/301 |
| 2009/0244533 A1 * | 10/2009 | Matousek | A61B 5/417 356/301 |
| 2010/0079754 A1 * | 4/2010 | Kuo | G01J 3/02 356/301 |
| 2011/0080580 A1 * | 4/2011 | Fermann | G01N 21/31 356/301 |
| 2012/0089030 A1 | 4/2012 | Guze et al. | |
| 2013/0022250 A1 * | 1/2013 | Nygaard | A61J 3/007 382/128 |
| 2013/0038869 A1 | 2/2013 | Lascola et al. | |
| 2013/0258877 A1 * | 10/2013 | Ji | H04B 7/0632 370/252 |
| 2014/0009826 A1 * | 1/2014 | Fukutake | G02B 21/16 359/385 |
| 2014/0103224 A1 * | 4/2014 | Ng | G01N 21/05 250/435 |
| 2014/0226158 A1 * | 8/2014 | Trainer | G02B 6/32 356/336 |
| 2014/0354989 A1 * | 12/2014 | Marbach | G01N 21/65 356/301 |
| 2016/0209388 A1 | 7/2016 | Yakovlev et al. | |

FOREIGN PATENT DOCUMENTS

| | | |
|---|---|---|
| DE | 32 23 876 C2 | 10/1985 |
| DE | 693 13 633 T2 | 4/1998 |
| DE | 11 2006 000 273 T5 | 1/2013 |
| DE | 10 2012 101 744 A1 | 9/2013 |
| WO | WO-98/22802 A1 | 5/1998 |
| WO | WO-2004/031749 A3 | 6/2004 |
| WO | WO-2015/114379 A1 | 8/2015 |

* cited by examiner

APPARATUS AND METHOD FOR BIDIRECTIONAL RAMAN SPECTROSCOPY

REFERENCE TO RELATED APPLICATION

This application is a continuation-in-part of U.S. application Ser. No. 15/461,613, entitled "LIGHT DELIVERY AND COLLECTION DEVICE FOR PERFORMING SPECTROSCOPIC ANALYSIS OF A SUBJECT", filed on Mar. 17, 2017, by Jun Zhao, Xin Jack Zhou, and Sean Xiaolu Wang, which is a continuation-in-part of U.S. application Ser. No. 15/378,156, entitled "LIGHT DELIVERY AND COLLECTION DEVICE FOR MEASURING RAMAN SCATTERING OF A SAMPLE", filed on Dec. 14, 2016, by Jun Zhao, Xin Jack Zhou, and Sean Xiaolu Wang, which is a continuation-in-part of U.S. application Ser. No. 15/349,510, entitled "LIGHT DELIVERY AND COLLECTION DEVICE FOR MEASURING RAMAN SCATTERING OF A SAMPLE", filed on Nov. 11, 2016, by Jun Zhao and Xin Jack Zhou. The subject matter of the aforementioned U.S. applications is hereby incorporated herein by reference.

FIELD OF THE INVENTION

This invention generally relates to apparatus and method for Raman spectroscopy, and more specifically to apparatus and method for bidirectional Raman spectroscopy.

BACKGROUND

Raman spectroscopy is an optical spectroscopy technique, which measures the inelastic scattering, i.e. Raman scattering of monochromatic light by a material to produce a spectrum characteristic of the material. Raman spectroscopy has been demonstrated to be a powerful non-invasive analytical technology for material characterization and identification.

Conventional Raman spectroscopy generally utilizes a focused laser beam to produce Raman scattering signal from the sample, where the back scattered Raman light is collected and measured with a spectrometer device. Although forward scattered Raman signal can be measured provided it is not completely blocked by the sample, it is not the favored approach in most situations. For transparent samples, the excitation light is much stronger in the forward scattered beam than in the back scattered beam, which makes it harder to be filtered out. For diffusely scattering samples, the Raman signal is attenuated much more strongly in the forward scattered beam than in the back scattered beam, which makes the measurement more time consuming. However, a major drawback of the back scattering geometry is that in diffusely scattering samples, the signal collected is primarily from the surface of the sample, which has shorter scattering path length for both the excitation light and the Raman light than from inside the sample. Thus, if multiple components are distributed in a diffusely scattering sample unevenly, the back scattered geometry will not produce results representative of the sample as a whole.

Transmission Raman measures the forward scattered Raman signal. As the light travels from the front surface to the back of the sample, the scattering path length increases for the excitation light but decreases for the Raman scattered light, such that the difference in contribution from different depths toward the total detected signal is much reduced. For this reason, transmission Raman is the preferred method in content uniformity measurements of pharmaceutical products despite its lower signal throughput. However, due to the complex nature of samples and the unpredictable scattering behavior of the excitation and Raman scattered light, even transmission Raman does not necessarily measure different depths with equal weights. Often, the sample orientation is changed and one or more additional measurements are made, and their average provides a better representation of the sample as a whole. This adds complexity to the measurement.

There thus exists a need for an improved apparatus and method for performing Raman spectroscopy, which not only allows the measurement of a large area of the sample but also enables sub-surface Raman signal collection with two excitation beams penetrating the sample in opposite directions, thereby producing the best possible representation of the sample as a whole without the need of reorienting the sample.

SUMMARY OF THE INVENTION

It is the object of the present invention to provide an apparatus and method for performing bidirectional Raman spectroscopy of a sample, preferably a diffusely scattering sample, in which two excitation light sources are employed to illuminate the sample from two opposite directions to excite Raman scattering signal from the sample. The Raman scattering signal which transmits through the sample are collected by two optical devices each positioned on the opposite side of the sample to obtain two transmission Raman spectra of the sample, which enables the accurate determination of the composition of the whole sample.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
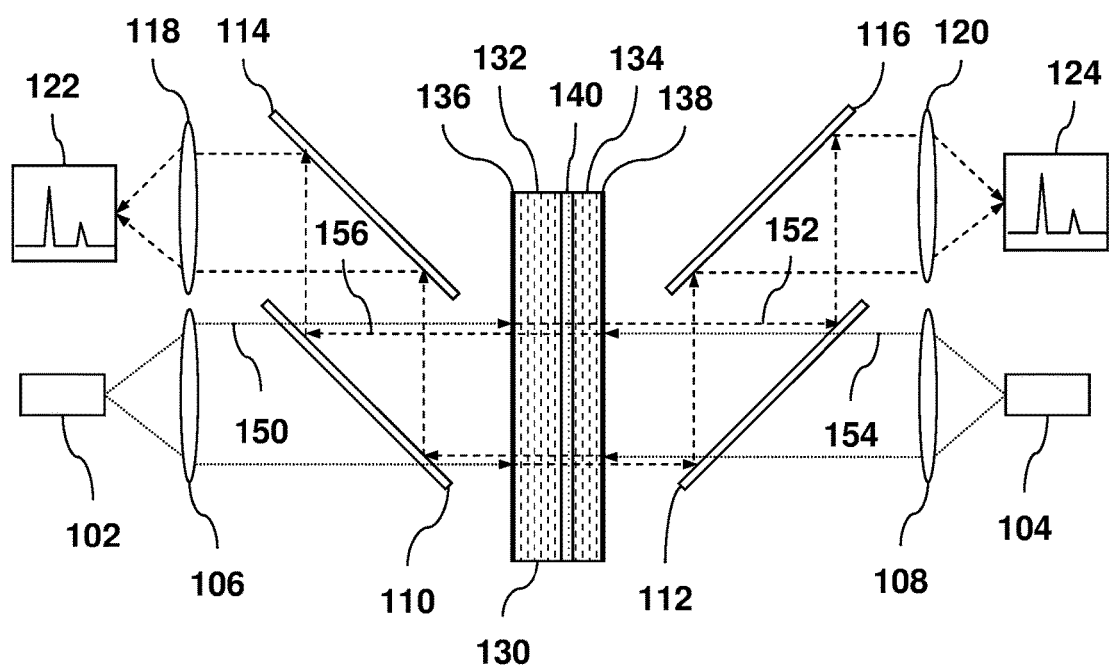
FIG. 1 illustrates a first exemplary embodiment of the bidirectional Raman spectroscopy apparatus.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to bidirectional Raman spectroscopy. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

FIG. 1 illustrates a first exemplary embodiment of the bidirectional Raman spectroscopy apparatus, which is utilized to measure the transmission Raman spectrum of a diffusely scattering sample 130, such as a multilayered pharmaceutical tablet. The Raman spectroscopy apparatus comprises two light sources 102 and 104, each positioned on the opposite side of the sample 130. The light sources are preferably laser light sources, and more preferably laser diode light sources with their output spectrum narrowed and stabilized by volume Bragg gratings (VBGs). The laser beams 150 and 154 produced by the two light sources 102 and 104 are first collimated by optical lenses 106 and 108 and then transmit through dichroic beam splitters 110 and 112, respectively to illuminate the sample 130 from two opposite directions. The laser beam 150 excites Raman scattered light 152 from the sample 130 which transmits through the sample 130. The Raman scattered light 152 is then reflected by the dichroic beam splitters 112 and optical mirror 116 and focused by optical lens 120 into an optical spectrometer 124 for spectral analysis. Similarly, the laser beam 154 excites Raman scattered light 156 from the sample 130, which transmits through the sample 130 and is then reflected by the dichroic beam splitters 110 and optical mirror 114 and focused by optical lens 118 into an optical spectrometer 122 for spectral analysis. The collimated laser beam has a relatively large beam diameter such that it excites Raman scattered light from a large area of the sample to make the measured Raman spectrum more representative. In addition, the intensity of the laser beam on the sample is reduced in comparison to a focused laser beam to avoid sample damage.

In this exemplary embodiment, the sample 130 is a multilayered diffusely scattering sample, e.g. a pharmaceutical tablet having two coating layers 136 and 138 and a middle layer 140 sandwiched between two inner layers 132 and 134. Taking the middle layer 140 as an example, there exists an optical path length difference in the excitation and transmission of the Raman signal from the middle layer 140 when the sample 130 is illuminated from the two opposite directions. When the sample 130 is illuminated from the left hand side by laser beam 150, the laser beam 150 first transmits through the coating layer 136 and the inner layer 132 and then excites Raman scattered light from the middle layer 140. The Raman scattered light from the middle layer 140 then transmits through the inner layer 134 and the coating layer 138 to be measured with the optical spectrometer 124. When the sample 130 is illuminated from the right hand side by laser beam 154, the laser beam 154 first transmits through the coating layer 138 and the inner layer 134 and then excites Raman scattered light from the middle layer 140. The Raman scattered light from the middle layer 140 then transmits through the inner layer 132 and the coating layer 136 to be measured with the optical spectrometer 122. Due to the wavelength difference between the laser light and the Raman scattered light, the coating layers 136 and 138 and the inner layers 132 and 134 may have different absorption and scattering coefficients for the laser light and the Raman scattered light. Therefore, the above mentioned optical path length difference will result in a difference in the measured Raman signal intensity for the middle layer 140 when the sample 130 is illuminated from the two opposite directions. This signal intensity difference is dependent on the location of the middle layer 140 in the sample 130. The more the middle layer 140 deviates from the center of the sample, the larger the intensity difference will be. In extreme cases, the signal intensity difference may become very large such that the Raman feature from the middle layer 140 is hard to be observed when the sample is measured from one specific direction. The dual illumination scheme as disclosed in the present invention will overcome this issue. When the absorption and scattering coefficients of the sample are known at the laser and Raman signal wavelength, it is possible to infer the location of the middle layer 140 inside the sample from the difference in its Raman signal intensity when measured from the two opposite directions. One possible way to obtain the absorption and scattering coefficient of the sample is to measure a transmission spectrum and a reflection spectrum of the sample at the wavelengths of interest.

In the scheme as disclosed in FIG. 1, the two optical spectrometers 122 and 124 may be configured to work simultaneously such that when the laser source 102 is turned on, the optical spectrometer 122 collects the back-scattered Raman light from the sample 130 and the optical spectrometer 124 collects the transmitted Raman light from the sample 130 to obtain a reflection Raman spectrum and a transmission Raman spectrum simultaneously, where the reflection Raman spectrum mainly contains the Raman features of the surface layer on the left-hand side of the sample (e.g. layer 136 and 132 of the sample 130) and the transmission Raman spectrum contains the Raman features of all layers of the sample. Similarly, when the laser source 104 is turned on, the optical spectrometer 124 collects the back-scattered Raman light from the sample 130 and the optical spectrometer 122 collects the transmitted Raman light from the sample 130 to obtain a reflection Raman spectrum and a transmission Raman spectrum simultaneously, where the reflection Raman spectrum mainly contains the Raman features of the surface layer on the right-hand side of the sample (e.g. layer 138 and 134 of the sample 130) and the transmission Raman spectrum contains the Raman features of all layers of the sample. These four Raman spectra may be analyzed simultaneously by a processor unit to investigate the composition of the surface layer and inner layer of the sample. For example, the composition of the surface layers may be inferred from the two reflection Raman spectra and the composition of the inner layers may be inferred from the difference of the two transmission Raman spectra in relation to the two reflection Raman spectra.

In a slight variation of the present embodiment, the two optical spectrometers 122 and 124 may be replaced with two separate channels of a single multichannel spectrometer or a single optical spectrometer switched sequentially using an optical switch to measure the transmitted Raman signals in the two opposite directions. The two laser beams may be from two separate lasers sources, or from a single laser source split by means of an optical beam splitter and separately switched on or off with an optical shutter. Alternatively, the two laser beams may be from the same laser source switched to illuminate the sample 130 in two opposite directions by an optical switch.

Figure 2:
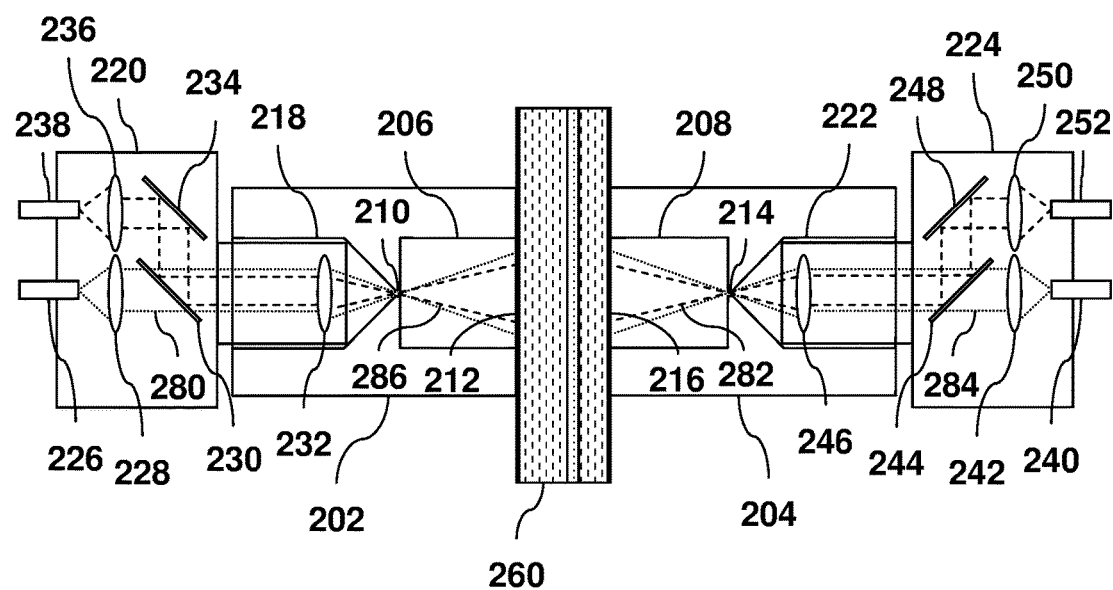
FIG. 2 illustrates a second exemplary embodiment of the bidirectional Raman spectroscopy apparatus.

FIG. 2 illustrates a second exemplary embodiment of the bidirectional Raman spectroscopy apparatus, in which the intensity of the transmission Raman signal is enhanced by a reflective cavity based light delivery and collection device. The light delivery and collection device is disclosed in U.S. patent application Ser. No. 15/461,613, U.S. patent application Ser. No. 15/378,156, and U.S. patent application Ser. No. 15/349,510, which are hereby incorporated herein by reference. Referring to FIG. 2, the bidirectional transmission Raman spectroscopy apparatus comprises two of such light delivery and collection devices 202 and 204, each positioned on the opposite side of a diffusely scattering sample 260. The light delivery and collection devices 202 and 204 each comprises a reflective cavity 206 and 208, which are made of a material having high reflectivity to the laser light and the Raman scattered light. Such material can be metal materials, e.g. gold, silver, copper, and aluminum, etc. The surface of the reflective cavity is preferably polished to produce specular reflection to the laser light and the Raman scattered light. Alternatively, the reflective cavity 206 and 208 may have a surface coating with high reflectivity to the laser light and the Raman scattered light. Such surface coating can be a metal coating which exhibits high reflection in a broad range of wavelengths. Or it can be a dielectric coating, which has a customized reflection wavelength range. The surface coating is preferably a smooth coating to produce specular reflection to the laser light and the Raman scattered light.

The light delivery and collection device 202 and 204 each comprises a receptacle 218 and 222 to receive a Raman probe 220 and 224, respectively. Each of the Raman probes 220 and 224 further comprises input optical fiber 226 and 240 for receiving excitation light 280 and 284 from a laser light source (not shown) as well as output optical fiber 238 and 252 for delivering the collected Raman light 286 and 282 into an optical spectrometer (not shown) for spectral analysis. Other optical components in the Raman probes 220 and 224 include optical lenses 228 and 242, 236 and 250, dichroic beam splitters 230 and 244, optical mirrors 234 and 248, which function in a similar way as the corresponding optical components shown in FIG. 1. The excitation light 280 and 284 from the optical fiber 226 and 240 is focused by optical lens 232 and 246 at a first aperture 210 and 214 of the reflective cavity 206 and 208 and thereby enters the reflective cavity 206 and 208, respectively. The aperture 210 and 214 preferably has a size as small as possible, but large enough to pass unobstructed the excitation light and the Raman light. The excitation light 280 and 284 diverges and projects onto a second aperture 212 and 216 of the reflective cavity 206 and 208, respectively, which preferably has a size much larger than the first aperture 210 and 214, and more preferably, at least two times as large as the first aperture 210 and 214 in area and covers an area of at least a few square millimeters. The second aperture 212 and 216 of the reflective cavity 206 and 208 is configured to be applied close to the sample 260 such that the reflective cavity 206 and 208 substantially forms an enclosure covering a large area of the sample 260, where the excitation light 280 and 284 enters and produces Raman scattered light 282 and 286 from the covered area of the sample 260, respectively. By collecting the Raman scattering from a large volume of the sample, the intensity of excitation light on the sample is reduced to avoid sample damage. In the meantime, the collected Raman spectrum is more representative, especially for non-uniform samples. Here the sample 260 can be diffusely scattering samples, such as pharmaceuticals, powders, biological tissues, etc. or even samples having multiple layers of different materials. The sample 260 reflects and/or scatters the excitation light 280 and 284, either through elastic scattering or inelastic scattering (i.e. Raman scattering and Brillouin scattering) back into the reflective cavity 206 and 208, respectively. The reflective cavity 206 and 208 reflects the excitation light that is reflected and/or back-scattered from the sample and redirects it towards the sample. This causes more excitation light to penetrate into the diffusely scattering sample to produce Raman scattering from the subsurface layer of the sample. In addition, the reflective cavity 206 and 208 reflects the Raman scattered light from the sample unless the Raman scattered light either emits from the first aperture 210 and 214 to be collected by the Raman probe 220 and 224, or re-enters the sample 260 and be re-scattered by the sample 260 at the second aperture 212 and 216. This multi-reflection process improves the collection efficiency of the Raman scattered light from the sample.

The Raman spectroscopy apparatus of FIG. 2 may work in a similar manner as the Raman spectroscopy apparatus of FIG. 1 to collect four Raman spectra of the sample 260, i.e. a reflection and a transmission Raman spectrum when the sample is illuminated from the left-hand side of the sample and a reflection and a transmission Raman spectrum when the sample is illuminated from the right-hand side of the sample. The four Raman spectra may be analyzed simultaneously by a processor unit to investigate the composition of the surface layer and inner layer of the sample.

Figure 3A:
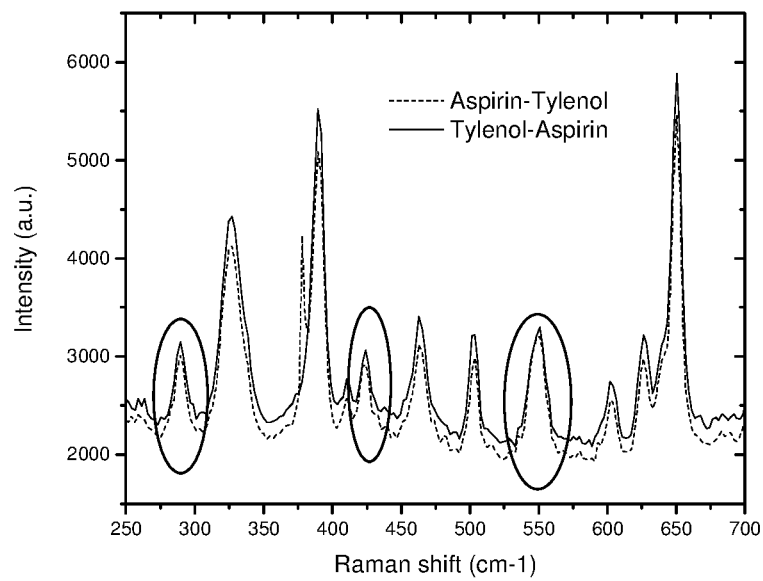
FIGS. 3A and 3B show a comparison of the transmission Raman spectra of a composite pharmaceutical tablet sample measured from two opposite directions.
Figure 3B:
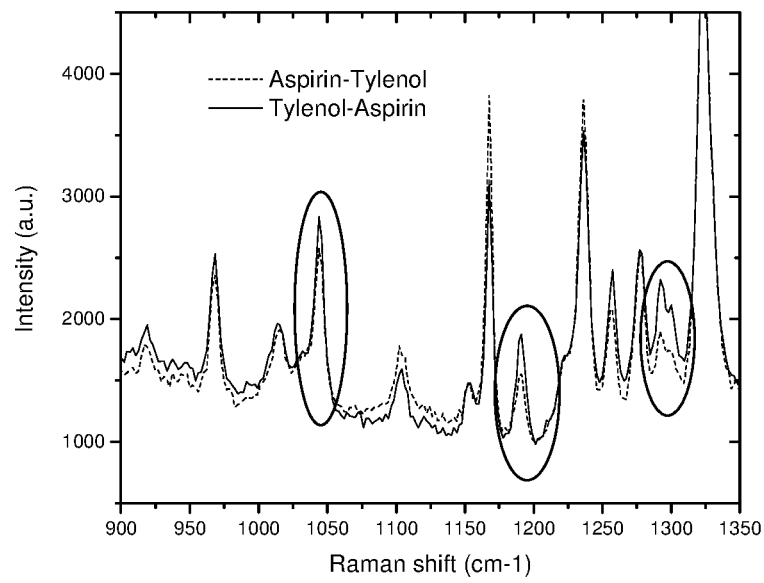

FIGS. 3A and 3B show a comparison of the transmission Raman spectra of a composite pharmaceutical tablet sample measured from two opposite directions. The composite tablet sample is composed of a Tylenol tablet on one side and an Aspirin tablet on the other side. The Raman spectrum in dashed line is measured when the laser light illuminates the sample from the Aspirin side and the Raman spectrum in solid line is measured when the laser light illuminates the sample from the Tylenol side. Checking the Raman bands of Aspirin (the circled Raman bands as shown in FIGS. 3A and 3B), it can be seen that when the Raman shift is small (as shown in FIG. 3A), the two spectra show almost the same intensity. But when the Raman shift is large (as shown in FIG. 3B), the Aspirin band shows higher intensity when the laser light illuminates the sample from the Tylenol side. One possible reason for this is that the laser light has lower absorption and scattering loss than the Raman light when their wavelength difference is large enough. Thus the transmission Raman spectra measured in two opposite directions not only provides the composition information of the tablet sample but also reveals the relative location of its ingredients (i.e. Tylenol and Aspirin in this example).

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. An apparatus for analyzing the properties of a diffusely scattering subject, the apparatus comprising:
   a first light source for producing a first excitation light;
   a first reflective cavity with a specular reflective surface, the first reflective cavity having a first aperture and a second aperture, the first aperture of the first reflective cavity is configured to receive the first excitation light, the second aperture of the first reflective cavity is configured to be applied close to the subject such that the first reflective cavity substantially forms an enclosure covering a first area of the subject, wherein the first excitation light projects from the first aperture onto the second aperture of the first reflective cavity to illuminates the first covered area of the subject from a first direction to excite a first Raman scattered light;
   a first optical device configured to measure a portion of the first Raman scattered light which transmits through the subject in the first direction to obtain a first Raman spectrum;
   a second light source for producing a second excitation light;
   a second reflective cavity with a specular reflective surface, the second reflective cavity having a first aperture and a second aperture, the first aperture of the second reflective cavity is configured to receive the second excitation light, the second aperture of the second reflective cavity is configured to be applied close to the subject such that the second reflective cavity substantially forms an enclosure covering a second area of the subject, wherein the second excitation light projects from the first aperture onto the second aperture of the second reflective cavity to illuminates the second covered area of the subject from a second direction opposite to the first direction to excite a second Raman scattered light;
   a second optical device configured to measure a portion of the second Raman scattered light which transmits through the subject in the second direction to obtain a second Raman spectrum; and
   a processor unit configured to analyze both the first Raman spectrum and the second Raman spectrum to analyze the properties of the subject.

2. The apparatus of claim 1, wherein the first optical device is configured to measure a portion of the second Raman scattered light which is scattered back from the subject to obtain a third Raman spectrum, and the second optical device is configured to measure a portion of the first Raman scattered light which is scattered back from the subject to obtain a fourth Raman spectrum.

3. The apparatus of claim 2, wherein the processor unit is configured to analyze the first, second, third, and fourth Raman spectra to analyze the properties of the subject.

4. The apparatus of claim 1, wherein the first optical device and the second optical device are two separate optical spectrometers.

5. The apparatus of claim 1, wherein the first optical device and the second optical device are two separate channels of a single multichannel optical spectrometer.

6. The apparatus of claim 1, wherein the first light source and the second light source are from the same light source split by an optical beam splitter and separately switched on or off.

7. The apparatus of claim 1, wherein the first light source and the second light source are from the same light source switched by an optical switch to illuminate the subject from the first direction and the second direction sequentially.

8. A method for analyzing the properties of a diffusely scattering subject, the method comprising the steps of:
   producing a first excitation light;
   providing a first reflective cavity with a specular reflective surface, the first reflective cavity having a first aperture and a second aperture, the first aperture of the first reflective cavity is configured to receive the first excitation light, the second aperture of the first reflective cavity is configured to be applied close to the subject such that the first reflective cavity substantially forms an enclosure covering a first area of the subject, wherein the first excitation light projects from the first aperture onto the second aperture of the first reflective cavity to illuminates the first covered area of the subject from a first direction to excite a first Raman scattered light;
   measuring a portion of the first Raman scattered light which transmits through the subject in the first direction to obtain a first Raman spectrum;
   producing a second excitation light;
   providing a second reflective cavity with a specular reflective surface, the second reflective cavity having a first aperture and a second aperture, the first aperture of the second reflective cavity is configured to receive the second excitation light, the second aperture of the second reflective cavity is configured to be applied close to the subject such that the second reflective cavity substantially forms an enclosure covering a second area of the subject, wherein the second excitation light projects from the first aperture onto the second aperture of the second reflective cavity to illuminates the second covered area of the subject from a second direction opposite to the first direction to excite a second Raman scattered light;
   measuring a portion of the second Raman scattered light which transmits through the subject in the second direction to obtain a second Raman spectrum; and
   analyzing the first Raman spectrum and the second Raman spectrum to analyze the properties of the subject.

9. The method of claim 8, further comprising the steps of:
   measuring a portion of the second Raman scattered light which is scattered back from the subject to obtain a third Raman spectrum;
   measuring a portion of the first Raman scattered light which is scattered back from the subject to obtain a fourth Raman spectrum; and
   analyzing the first, second, third, and fourth Raman spectra to analyze the properties of the subject.

10. The method of claim 8, wherein the first Raman spectrum and the second Raman spectrum are measured by two separate optical spectrometers.

11. The method of claim 8, wherein the first Raman spectrum and the second Raman spectrum are measured by two separate channels of a single multichannel optical spectrometer.

12. The method of claim 8, wherein the first excitation light and the second excitation light are produced by two separate light sources.

13. The method of claim 8, wherein the first excitation light and the second excitation light are produced by the same light source split by an optical beam splitter and separately switched on or off.

14. The method of claim 8, therein the first excitation light and the second excitation light are produced by the same light source switched by an optical switch to illuminate the subject from the first direction and the second direction sequentially.

\* \* \* \* \*